United States Patent [19]

Stendel et al.

[11] Patent Number: 4,965,287

[45] Date of Patent: Oct. 23, 1990

[54] METHOD FOR CONTROLLING PARASITOSIS IN BEES

[75] Inventors: Wilhelm Stendel, Wuppertal; Hubert Neuhauser, Bergisch-Gladbach; Nikolaus Koeniger, Oberursel, all of Fed. Rep. of Germany

[73] Assignee: Bayer Aktiengesellschaft, Leverkusen, Fed. Rep. of Germany

[21] Appl. No.: 318,041

[22] Filed: Mar. 2, 1989

Related U.S. Application Data

[63] Continuation of Ser. No. 922,636, Oct. 24, 1986, abandoned.

[30] Foreign Application Priority Data

Oct. 31, 1985 [DE] Fed. Rep. of Germany ....... 3538688

[51] Int. Cl.$^5$ ............................................ A61K 31/215
[52] U.S. Cl. ................................... 514/531; 514/532; 514/538; 449/2
[58] Field of Search ...................... 514/531, 532, 538; 449/2

[56] References Cited

U.S. PATENT DOCUMENTS 4,276,306 6/1981 Fuchs et al. .................... 514/531
4,646,377 3/1987 Ritter ............................. 449/2

OTHER PUBLICATIONS

Nijhuis et al., Die Biene, vol. 2, p. 55–56 (1985).
Chem. Abstracts, vol. 95, 42696y (1981).
Shires, Pesticide Science, vol. 16(2), p. 205 (1985-Apr.).
Le Blanc, Pesticide Science, vol. 16(2), p. 206 (1985-Apr.)
Gerig, Pesticide Science, vol. 16(2), p. 206–207 (1985-Apr.)
Delabie et al., Pesticide Science, vol. 16(4), p. 409–415 (1985).

*Primary Examiner*—John M. Ford
*Assistant Examiner*—Bernard L. Dentz
*Attorney, Agent, or Firm*—Sprung, Horn, Kramer & Woods

[57] ABSTRACT

In the control of parasitoses in honey bees by applying to the bees, their food or their habitat a parasiticide which is selectively active against such parasitoses but not against said bees, the improvement wherein such parasiticide is a synthetic pyrethroid.

12 Claims, No Drawings

METHOD FOR CONTROLLING PARASITOSIS IN BEES

This is a continuation, of application Ser. No. 922,636, filed Oct. 24, 1986, now abandoned.

The present invention relates to a new method for controlling parasitosis in honey bees and to agents for carrying out this method.

Parasites which harm bees are known. In particular, there is an increase in the harm caused by mites on all stages of development of honey bees. A particular problem in this context is represented by *Varroa jacobsoni*. The harm caused by it has now become spread virtually world-wide. Without suitable protective measures, the colonies which are affected die.

It is known to control parasitosis by fumigation of the bee colonies with formic acid of with bromopropylate (isopropyl 4,4'-dibromobenzilate). It is furthermore known to carry out treatments with coumaphos O,O-diethyl O-(3-chloro-4-methylcoumarin-7-yl) thionophosphate (U.S. application Ser. No. 670,718, filed Nov. 13, 1984). It has also been disclosed to use pyrethrum extracts for control (Die Biene 2/1985, page 55). Although these agents are effective they are also toxic to bees.

It has now been found that parasitosis in honey bees can be controlled very successfully by synthetic pyrethroids.

Synthetic pyrethroids are among the most effective insecticides of all. They are considerably more effective than the pyrethrum extracts obtained from plants. Thus, it was extremely surprising that it was possible to use them for treatment of parasitosis in honey bees without harming the honey bees at the same time.

The synthetic pyrethroids include compounds of the formula I

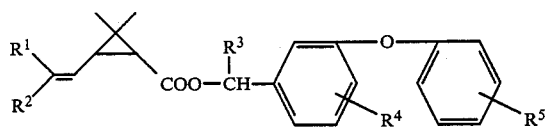

in which
$R^1$ represents halogen,
$R^2$ represents halogen, alkyl which is optionally halogen-substituted, and phenyl which is optionally halogen-substituted,
$R^3$ represents hydrogen or CN,
$R^4$ represents hydrogen or halogen, and
$R^5$ represents hydrogen or halogen.

Preferred synthetic pyrethroids of the formula I are those in which
$R^1$ represents halogen, in particular fluorine, chlorine and bromine,
$R^2$ represents halogen, in particular fluorine, chlorine, bromine, trihalogenomethyl, phenyl and halogenophenyl,
$R^3$ represents hydrogen or CN,
$R^4$ represents hydrogen or fluorine, and
$R^5$ represents hydrogen.

Particularly preferred synthetic pyrethroids of the formula I are those in which
$R^1$ represents chlorine,
$R^2$ represents chlorine, trifluoromethyl or p-chlorophenyl,
$R^3$ represents CN,
$R^4$ represents hydrogen or fluorine, and
$R^5$ represents hydrogen.

Special mention maybe made of compounds of the formula I in which
$R^1$ represents chlorine,
$R^2$ represents chlorine or p-chlorophenyl,
$R^3$ represents CN,
$R^4$ represents fluorine in the 4-position, and
$R^5$ represents hydrogen.

The following synthetic pyrethroids may be mentioned specifically: permethrin, cypermethrin, cyfluthrin, cyhalothrin, deltamethrin and flumethrin.

Particular attention may be drawn to cyfluthrin (i.e. alpha-cyano-3-phenoxy-4-fluorobenzyl 3-(2,2-dichlorovinyl-2,2-dimethyl-cyclopropane carboxylate) and flumethrin. Special mention may be made of flumethrin, α-cyano-3-phenoxy-4-fluoro-benzyl 3-[2-(4-chlorophenyl)-2-chlorovinyl]-2,2-dimethyl-cyclopropane-carboxylate.

The active compounds exist in the form of their optical and steric isomers and in the form of mixtures of these isomers.

The active compounds are known (U.S. Pat. Nos. 4,218,469, 4,261,920, U.S. application Ser. No. 391,732, filed Jun. 24, 1982, now U.S. Pat. No. 4,611,009, DE-OS German Published Specifications Nos. 2,326,077 and 2,738,150).

Parasitosis in honey bees are those caused by the following parasites: *Varroa jacnbsoni, Acarapis woodi, Tropilaelaps clareae, Tropilaelaps koenigerum, Braula coeca, Galleria mellonella* (wax moth) and *Achroia grisella* (lesser wax moth).

The parasite which may be particularly mentioned is *Varroa jacobsoni*. This parasite directly harms the stages of development of the bees on which it multiplies. It also harms adult bees. However, it may also be responsible as a vector for other bee diseases.

The treatment of the honey bees can be carried out in a variety of ways, as follows:

1. by direct contact with the active compound. For this purpose the latter is, for example, sprayed, dusted, converted into a smoke, vaporized, volatilized or incorporated in carriers which come into contact with bees, or applied to the carriers, 2. through the social exchange of food in the bee colony and through a systemic action via the haemolymph of the bees. For this purpose the active compound is offered, for example, with the food or drinking water, or is poured or sprayed into the beehive.

In principle, the treatment can be carried out throughout the year. If the active compound is sprayed, dusted or converted into a smoke it is advantageous to carry out the treatment in the period when there is little or no brood. If the active compound is vaporized, volatilized or incorporated in carriers the treatment is preferably carried out throughout the year.

In case 2 (above), the treatment is particularly advantageously carried out at the time when the winter feed is given or in the period without brood.

It is also possible to treat the bee colony as an artificial swarm. This can also be carried out during the brood period.

Agents which are sprayed contain the active compound in concentrations of 0.1–25% by weight, preferably of 0.3–10% by weight.

These agents are preferably used either directly or after further dilution, preferably with water. When the agents are used directly application by the ultra low volume (ULV) method is preferred using customary equipment suitable for this purpose. The agents can also be sprayed with the assistance of electrostatic charging.

Before use, the agents can be diluted to active compound concentrations of $10^{-11}$–2% by weight, preferably $10^{-7}$–0.05% by weight. They are sprayed conventionally using customary equipment, such as knapsack sprayer, piston pump or paint spray gun.

Depending on the application method chosen, between 1 μg–30 mg, preferably 1 μg–10 mg, of active compound in the form of the agents, diluted where appropriate, are used per colony.

These agents are used to treat either the bees or the bee home or parts thereof.

The agents contain the active compound in addition to diluents and/or emulsifiers which are tolerated by the bees in the concentrations used.

Suitable diluents are alcohols, such as methanol, ethyl alcohol, tropanol, isopropyl alcohol, n-butyl alcohol, amyl alcohol and octanol; glycols, such as propylene glycol, 1,3-butylene glycol, ethylene glycol, dipropylene glycol monomethyl ether; diethylene glycol monomethyl ether; glycerol; aromatic alcohols, such as benzyl alcohol; carboxylic esters such as, for example, ethyl acetate, benzyl benzoate, butyl acetate, propylene carbonate and ethyl lactate; aliphatic hydrocarbons, oils such as, for example, cottonseed oil, groundnut oil, maize kernel oil, olive oil, castor oil and sesame oil; ketones such as, for example, acetone and methyl ethyl ketone; synthetic mono- and triglycerides with natural fatty acids.

Other very suitable diluents include compounds such as dimethyl sulphoxide, dimethylacetamide, dimethylformamide, N-methylpyrolidone, dioxane and 2-dimethyl-4-oxymethyl-1,3-dioxalane.

Particularly suitable are lower alcohols having up to 8 carbon atoms in the molecule, as well as lower ketones such as methyl ethyl ketone and ethers of ethylene glycol and of propylene glycol.

In the preparation of the agents which can be used according to the invention it is possible to use one or more diluents.

Suitable emulsifiers are: anionic surfactants, such as Na lauryl sulphate, fatty alcohol ether sulphates, mono/dialkylpolyglycol ether orthophosphoric ester-monoethanolamine salt, and calcium alkylarylsulphonate, cationic surfactants such as cetyltrimethylammonium chloride, ampholytic surfactants such as di-Na N-lauryl-:-iminodipropionate or lecithin, non-ionic surfactants, for example polyoxyethylated castor oil, polyoxyethylated sorbitan monooleate, sorbitan monostearate, glycerol monostearate, polyoxyethylene stearate and alkylphenol polygylcol glycol ethers.

Preferred emulsifiers which may be mentioned are: non-ionic, water-soluble emulsifiers with a HLB (hydrophilic/lipophilic/balance value) greater than 10, for example emulsifier NP 10® (Bayer AG), alkylaryl polyglycol ethers; Renex 678 ® (Atlas Chemical Industries), polyoxyethylene alkylaryl ethers; Tween 40® (Atlas), polyoxyethylene sorbitan monopalmitate; Myri 53® (Atlas), polyoxyethylene stearate; Atlas G 3707 ®, polyoxyethylene lauryl ether; Atlas G 3920 ®, polyoxyethylene oleyl ethers; Atlas G 9046®, polyoxyethylene mannitan monolaurate; emulsifier 1371 B ® (Bayer AG), alkyl polyglycol ethers; emulsifier 1736® (Bayer AG), alkyl polyglycol ethers (oleyl polyglycol ethers); emulsifier 0 X ® (Bayer AG), alkyl polyglycol ethers (dodecyl polyglycol ethers); Ninox BM-2® (Stepan Chemical Co.), ethoxylated nonylphenol; Triton X-100 ® (Rohm and Haas Co.), isooctylphenol-polyethoxyethanol; Cremophor EL ®, polyoxyethylated castor oil.

The agents according to the invention contain the emulsifiers in concentrations of 0–10 times, preferably 0–5 times, that of the active compound use. The diluents are added to make up to the desired final concentration in each case.

The agents are prepared by dissolving the active compound or compounds in the solvent or in an emulsifier or emulsifier/solvent mixture, if necessary with heating. The agents are further diluted with water, if required, to the desired concentration.

The agents for dusting contain the active compound in addition to conventional carriers which are tolerated by bees and are suitable for the preparation of dusting powders or wettable powders.

Examples of suitable carriers are inorganic carriers such as talc, kaolin, calcium carbonate, silicates, bentonites, as well as organic carriers such as, for example, starches, for example rice starch, sugars, cellulose and cellulose derivatives.

The agents are prepared, where appropriate with the addition of wetting agents, by mixing the active compound or compounds with the carriers. Examples of suitable wetting agents are the emulsifiers listed above.

Agents which are converted into a smoke contain the active compound in concentrations of $10^{-7}$–2% by weight per 100 g of carrier. The carrier used is the material customary for products for fumigation.

Examples of agents which are used to vaporize the active compound are carriers which are impregnated with agents containing active compound or into which the active compound is incorporated. Small plates or films made of paper, cardboard, cellulose, cloth, felt, fabric or leather, which are impregnated with agents containing active compound and are heated by a heat source are preferred. Mention may be made as the heat source of the small electric or battery-driven vaporizer ovens customary for small vaporizer plates.

It is particularly advantageous to use agents into which the active compound has been incorporated or onto which it has been applied and which act without an additional heat source. The treatment can be carried out particularly straightforwardly with these. The agents are simply introduced into the beehive. The colony experiences no upset as with spraying, fumigating or dusting.

The treatment is terminated by removal of the agent. This prevents the mites being exposed to continuously decreasing concentrations of active compound. This prevents the development of resistance in the mites.

The long-lasting release of active compound from these agents permits long-term therapy which also deals with the mite offspring from the bee brood.

Depending on the period of development of the parasites and of the bees the treatment can be specifically carried out such that either the entire mite brood from worker combs or the entire mite brood from drone combs is dealt with. For this purpose, the agents remain for 12–90, preferably 12–20, days in the beehive.

Hence, it is unnecessary to carry out the treatment in the time when there is no brood or little brood, or artificially to ensure that there is no brood in the colony before the treatment.

Contamination of the honey with active compound is virtually ruled out if the treatment is carried out outside the honey harvesting time.

With these agents the active compound can be contained or incorporated in carriers or be applied, in a suitable form, to carriers.

Carriers are shaped articles which are placed on or in the beehive. It is also possible for parts of the beehive to be formed of material into which the active compound has been incorporated or onto whose surface the active compound has been applied or which has been impregnated or soaked with active compound. Partitions which are inserted between the combs and have been treated with agents containing active compound or into which the active compound has been incorporated are preferred.

The carriers which can be used are natural or synthetic carriers. Examples of natural carriers are wood, wood-processing products, cardboard, paper, vulcanized or unvulcanized rubber, felt, metal, glass, porcelain and ceramic materials. Examples of synthetic carriers are plastics based on polyvinyl, PVC, polyacrylate, polymethacrylate, epoxide, polyurethane, polyester, polyamide, cellulose and its derivatives, polyethylene and polypropylene, and synthetic rubber.

However, suitable carriers are also coatings which have been applied to a rigid or flexible substrate. Coatings of this type may be absorbent and be treated with agents containing active compound. However, they can also be non-absorbent and contain the incorporated active compound. As a rule, these coatings are adherent polymers to which, where appropriate, inert fillers have been added. The polymers which are used for this purpose are the surface coating raw materials of the paints industry and, for example, cellulose derivatives, acrylates and methacrylates.

Examples of fillers for the production of absorbent coatings which may be mentioned are: kaolin, calcium carbonate, silicates, bentonites, cellulose, cellulose derivatives, starch and sawdust. In these cases the active compound is either already incorporated in the material forming the coating, or the coating is subsequently impregnated or soaked or sprayed, for example with the agent described above for spraying.

Coatings which contain the incorporated active compound can also be formed by paints or surface coatings containing active compound. These contain the active compound in a concentration of 0.00001-1, preferably 0.001-10, per cent by weight, in addition to the customary coating base. Dispersion paints and surface coatings are preferably used as the coating base.

However, it is also possible for coatings which contain the incorporated active compound to be films, strips and tapes, which are designed to be mono- or multi-layered and, where appropriate, self-adhesive.

Thus, it is possible for a self-adhesive film containing active compound, for example to consist of an adhesive layer, a flexible support layer, a flexible support layer containing active compound, and a flexible covering layer containing no active compound. The individual layers consist of polymeric materials which are known per se and which are suitable for the production of layers of this type.

As already mentioned, these shaped articles can contain the incorporated active compound. They contain the active compound in concentrations of 0.00001-10% by weight, preferably 0.00001-1% by weight, based on the base material of the shaped article.

Suitable shaped articles are strips, tapes and sheets, but also, as mentioned above, structural components of the beehive.

It is possible to use for the production of the shaped articles according to the invention polyvinyl resins, polyacrylates, epoxy resins, cellulose, cellulose derivatives, polyamides and polyesters which are sufficiently compatible with the abovementioned active compounds. The polymers need to have adequate strength and flexibility in order not to tear or become flawed during shaping. They must permit adequate migration of the active compounds to the surface of the shaped article.

Examples of typical vinyl resins are polyvinyl halides, such as polyvinyl chloride, polyvinyl chloride/vinyl acetate and polyvinyl fluoride; polyacrylate and polymethacrylate esters, such as poly(methyl acrylate) and poly(methyl methacrylate); and polyvinylbenzenes, such as polystyrene and polyvinyltoluene.

The plasticizers suitable for the production of the shaped articles, according to the invention, based on polyvinyl resin are those which are customarily used for plasticizing rigid vinyl resins. The plasticizer used depends on the resin and its compatibility with the plasticizer. Examples of suitable plasticizers are esters of phosphoric acid, such as tricresyl phosphate, esters of phthalic acid, such as dimethyl phthalate and dioctyl phthalate, and esters of adipic acid, such as diisobutyl adipate. However, it is also possible to use other esters, such as the esters of azelaic acid, maleic acid, ricinoleic acid, myristic acid, palmitic acid, oleic acid, sebacic acid, stearic acid and trimellitic acid, as well as complex linear polyesters, polymeric plasticizers and epoxidized soy bean oils. The amount of the plasticizer is about 10 to 50% by weight, preferably about 20 to 45% by weight, of the total composition.

The shaped articles can also contain other constituents such as stabilizers, lubricants, fillers and coloring materials without this changing the basic properties of the composition. Suitable stabilizers are antioxidants and agents which protect the shaped article from ultraviolet radiation and undesired disintegration during processing, such as extrusion. Some wetting agents, such as epoxidized soy bean oils, also serve as secondary plasticizers. Examples of lubricants which can be used are stearates, stearic acid and low molecular-weight polyethylene. These constituents can be used in a concentration of up to about 20% by weight of the total composition.

The production of the shaped articles, according to the invention, based on vinylic acid entails the various constituents being mixed dry by known mixing processes and being shaped by known extrusion or injection molding processes.

The choice of the processing method for the production of the shaped articles according to the invention is governed, on technical principles, by the rheological properties of the material of the shaped article and the shape of the desired structure. The processing methods can be adjusted to suit the processing technique or the type of shaping. In the case of the processing technique, the processes can be subdivided according to the rheological states through which they pass. Accordingly, suitable for viscous materials for shaped articles are casting, pressing, injection molding and spreading, and for viscoelastic polymers injection moulding, extrusion, calendering, rolling and, where appropriate, folding. Classified according to the type of shaping, the shaped articles according to the invention can be produced by casting, dipping, pressing, injection molding, extrusion, calendering, stamping, bending, deep-drawing etc.

These processing methods are known and require no further explanation. In principle, the statements made above for polyvinyl resins by way of example apply to polymers such as polyamides and polyesters.

Examples of agents which act via the social exchange of food in the bee colony are foodstuffs which contain the active compound. The following may be mentioned: granulated sugar and sugar-containing mixtures, solutions, suspensions or emulsions. These contain the active compound in concentrations of 0.5–20% by weight, preferably of 1–10% by weight. These mixtures are further diluted with water or sugar solution to use concentrations of the active compound of $10^{-8}$–1% by weight, preferably 0.0001–0.01% by weight, particularly preferably to 0.0001–0.005% by weight.

Their preparation is described in, for example, U.S. application Ser. No. 670,718 filed Aug. 13, 1984, now pending.

EXAMPLE A

Partitions (perforated plywood boards which are suspended in the beehive between the honeycombs, of 1553 cm$^2$) were painted on each side with 10 ml of a solution of 0.000239 g of flumethrin in 20 ml of n-hexane per partition. The partitions were dried at 34° C. for 24 hours and then suspended in beehive which contained bee colonies which were infested with *Varroa jacobsoni*. 2 treated partitions were suspended in each beehive. Untreated partitions were used as controls. At the end of the test the entire bee colony was killed in order to detect any surviving Varroa. The following results were obtained:

|  | Number of bees | Number of Varroa killed after 1 day | Number of Varroa killed after 2–12 days | Number of Surviving Varroa | Efficiency |
|---|---|---|---|---|---|
| Colony No. |  |  |  |  |  |
| 1 | 13,700 | 172 | 29 | 4 | 98% |
| 2 | 14,410 | 170 | 9 | 0 | 100% |
| 3 | 9,900 | 230 | 18 | 1 | 99% |
| Control |  |  |  |  |  |
| a | 12,500 | 1 | 13 | 273 |  |
| b | 13,720 | 0 | 5 | 98 |  |
| c | 8,910 | 2 | 7 | 431 |  |

EXAMPLE B

About 25 bees which were infested by *Varroa jacobsoni* and had recently been taken from a colony were treated in a wire cage by spraying with aqueous active compound solutions of different concentrations. The insects received an aqueous sugar solution as food. The numbers of bees and the numbers of Varroa which died during the test (2 days) were counted. After 2 days, the bees were killed in order to detect Varroa which still survived. The mortality of the Varroa and of the bees was determined.

|  |  | Mortality in % | |
|---|---|---|---|
| Active compound | Concentration | Varroa | Bees |
| Mixture of natural pyrethrins with | 0.005 | 25 |  |
|  | 0.01 | 58 | 19 |
| piperonylbutoxide (Spruzit ®) | 0.05 | 68 | 26 |
|  | 0.08 | 67 |  |
|  | 0.1 | 72 | 62 |
|  | 0.05 | 100 | 100 |
| Control |  | 23 | 5 |
| Flumethrin | 0.0001 | 100 | 6 |
|  | 0.001 | 100 | 37 |
|  | 0.01 | 100 | 86 |
| Control |  | 7 | 5 |

EXAMPLE 1

| Flumethrin |  | 2 g |
| --- | --- | --- |
| Emulsifier Toximul R ® | Mixture of Ca alkylbenzenesulphonate and non-ionic emulsifiers (HLB value: >10) | 7 g |
| Emulsifier Toximul S ® | Mixture of Ca alkylbenzenesulphonate and non-ionic emulsifier (HLB value: >10) | 5 g |
| Solvesso 200 ® | (Alkylnaphthalene mixture of high-boiling petroleum fractions | to 100 ml |

EXAMPLE 2

| Flumethrin |  | 1.6 g |
| --- | --- | --- |
| Emulsifier 368 ® | Alkylaryl polyglycol ether (molecular weight) about 1165) | 9 g |
| Emulsifier N P 10 ® | Nonylphenol polyglycol ethers | 9 g |
| Dimethylformamide |  | 10 g |
| Solvesso 200 |  | to 100 ml |

EXAMPLE 3

| Flumethrin |  | 0.5 g |
| --- | --- | --- |
| Emulsifier Atlox ® | Mixture of polyoxyethylene ethers, polyoxyglyceride, alkylarylsulphonate - very readily soluble in water) | 4 g |
| Emulsifier Atlox 3404 ® | (Mixture of polyoxyethylene alkylaryl ethers, alkylarylsulphonate - forms emulsion in water) | 2 g |
| Emulsifier Atlox 3409 ® | (Mixture of non-ionic and anionic emulsifiers- soluble in water) | 4 g |
| Solvent PC 2 | (high-boiling aromatic petroleum fraction) | to 100 ml |

EXAMPLE 4

| Flumethrin |  | 0.1 g |
| --- | --- | --- |
| Emulsifier 368 |  | 30 g |
| Dowanol DPM ® | (dipropylene glycol methyl ether) | to 100 ml |

EXAMPLE 5

| Flumethrin | 0.25 g |
|---|---|
| Emulsifier 368 | 10 g |
| Emulsifier NP 10 | 10 g |
| Solvesso 200 | 20 g |
| Dowanol DPM | to 100 ml |

EXAMPLE 6

| Flumethrin | 0.2 g |
|---|---|
| Emulsifier 368 | 9 g |
| Emulsifier NP 10 | 9 g |
| Solvesso 200 | 16 g |
| Dowanol DPM | 45 g |
| Water | to 100 ml |

EXAMPLE 7

| Flumethrin | 0.1 g |
|---|---|
| Emulsifier 368 | 10 g |
| Emulsifier NP 10 | 10 g |
| Solvesso 200 | 10 g |
| Dowanol DPM | to 100 ml |

EXAMPLE 8

| Flumethrin | | 0.25 g |
|---|---|---|
| Emulsifier Tween 80 ® | (sorbitan monooleate with HLB value: 4.5) | 8 g |
| Emulsifier Span 80 ® | (sorbitan monooleate with HLB value: 15) | 4 g |
| N-Methylpyrrolidone | | to 100 ml |

EXAMPLE 9

| Flumethrin | | 0.1 g |
|---|---|---|
| Cremophor HS 15 ® | (polyoxyethylene 600 hydroxystearate) | 20 g |
| Chlorobenzene | | to 100 ml |

EXAMPLE 10

| Flumethrin | | 0.1 g |
|---|---|---|
| Emulsifier W ® | (alkylaryl polyglycol ethers, molecular weight about 853) | 90 g |
| Dimethylisosorbitol | | to 100 ml |

EXAMPLE 11

| Active compound: | Flumethrin | 0.5 g |
|---|---|---|
| Wetting agent: | Emulvin W ® (alkylaryl polyglycol ethers) | 3.0 g |
| | Water | to 100 ml |

EXAMPLE 12

| Active compound: | Flumethrin | 5.0 g |
|---|---|---|
| Wetting agent: | as Example 1 | 30.0 g |
| | Water | to 100 ml |

EXAMPLE 13

| Active compound: | Flumethrin | 2.0 g |
|---|---|---|
| Wetting agent: | NP 10 ® (alkylaryl polyglycol ethers) | 40.0 g |
| | Water | to 100 ml |

EXAMPLE 14

| Active compound: | Flumethrin | 5.0 g |
|---|---|---|
| Wetting agent: | Emulsifier SZZ 14 ® | 20.0 g |
| | Water | 5.0 g |
| Solvent: | Isopropanol | to 100 ml |

EXAMPLE 15

1 g of flumethrin is thoroughly mixed with 99 g of talc. 5 g of this mixture are thoroughly mixed with 95 g of talc.

PREPARATION OF EMULSION CONCENTRATES

EXAMPLE 16

| 100% flumethrin | 25.00 g |
|---|---|
| Non-ionic emulsifier (emulsifier 368 ®) | 25.00 g |
| Dipropylene glycol monomethyl ether | to 100 ml |

The substances are weighed together and stirred until a clear solution has been produced.

The solution is diluted to its use concentration before use.

EXAMPLE 17

| 100% flumethrin | 1.00 g |
|---|---|
| Polyoxyethylene stearate | 0.50 g |
| Sorbitan sesquivleate | 0.40 g |
| Water | 4.00 g |
| Polyethylene glycol 200 | to 100 ml |

Preparation and use as for Example 16.

PREPARATION OF SMALL VAPORIZER PLATES

EXAMPLE 18

20 mg of flumethrin are dissolved in 100 ml of solvent ethanol.

An appropriate commercially available small filter board plate is impregnated with 0.5 ml of this solution. (The size of the small plate depends on the vaporizing device selected). The solvent is removed from these small plates by drying, and they contain 0.1 mg of flumethrin per small plate.

PRODUCTION OF A SHAPED PVC ARTICLE

EXAMPLE 19

| Flumethrin | 0.5 g |
|---|---|
| Isobutyl adipate | 15.5 g |

| | |
|---|---|
| -continued | |
| Dialkyl pythalate | 8.0 g |
| Polyoxyethylated castor oil | 2.0 g |
| Stearic acid | 0.8 g |
| Colorant | 0.1 g |
| Polyvinyl chloride | 73.1 g |
| | 100.0 g |

100.0 kg of this mixture are homogeneously mixed in a mixer, in the customary procedure for plasticized PVC.

This mixture is processed to a comb partition in an injection molding machine. Weight of the partition: 86.0 g.

The above mixture is prepared with 0.25 g of active compound in place of 0.5, and is rolled out in an appropriate calendering device to give a VM plate of the size of a DIN A4 sheet. The plate weighs 50.0 g. The sheet is placed in the beehive.

PRODUCTION OF A COATED CARRIER

EXAMPLE 20

A solution of flumethrin in emulsifier Span 20® Atlas and ethanol is uniformly applied, using a doctor knife, to a plate of 2 mm-thick polyethylene. The solution is adjusted so that 1 mg of flumethrin is applied per 100 cm² of surface and 0.5 mg of emulsifier is applied per 100 cm². The solvent is evaporated off, and the plate is punched out in a shape which can fit easily into the beehive.

PRODUCTION OF AN IMPREGNATED CARRIER WITH POLYMER (=SURFACE COATING) ADDITION

EXAMPLE 21

Aluminum foils coated with kieselguhr are treated with a solution of flumethrin and polyvinyl alcohol in such a manner that, after drying, 5 mg of flumethrin and 20 mg of polyvinyl alcohol remain on each 100 cm² of the foil.

The carrier shapes of the last two examples can be provided with an adhesive. After the adhesive protector has been removed they can be easily glued into empty partitions.

PRODUCTION OF GRANULES FOR USE WITH SOCIAL EXCHANGE OF FOOD

EXAMPLE 22

0.5 kg of flumethrin is dissolved in 7.5 l of ethanol, heating cautiously, and the solution is poured onto 99.5 kg of sugar in a mixing granulator while the mixer is running. The sugar which is moist with alcohol and is uniformly impregnated is dried and, where appropriate, screened. Before use, 1.0 g of the granules is dissolved in a sugar solution which is used to feed the bees.

It will be understood that the specification and examples are illustrative but not limitative of the present invention and that other embodiments within the spirit and scope of the invention will suggest themselves to those skilled in the art.

What is claimed:

1. In the control of parasitosis in honey bees by applying to the bees, their food or their habitat a parasiticide which is selectively active against such parasitosis but not against said bees, the improvement wherein such parasiticide is a synthetic pyrethroid.

2. The method according to claim 1, wherein such synthetic pyrethroid is of the formula

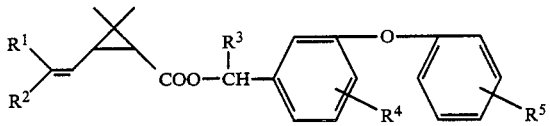

in which
$R^1$ represents halogen,
$R^2$ represents halogen, alkyl which is optionally halogen-substituted, and phenyl which is optionally halogen-substituted,
$R^3$ represents hydrogen or CN,
$R^4$ represents hydrogen or halogen, and
$R^5$ represents hydrogen or halogen.

3. The method according to claim 1, wherein such synthetic pyrethroid is of the formula

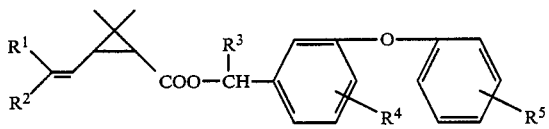

in which
$R^1$ represents halogen,
$R^2$ represents halogen, trihalogenomethyl, phenyl or halogenophenyl,
$R^3$ represents hydrogen or CN,
$R^4$ represents hydrogen or fluorine, and
$R^5$ represents hydrogen.

4. The method according to claim 1, wherein such synthetic pyrethroid is of the formula

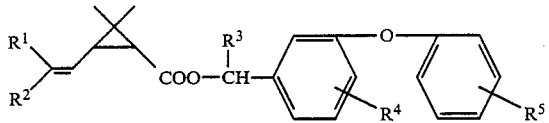

in which
$R^1$ represents chlorine,
$R^2$ represents chlorine, trifluoromethyl or p-chlorophenyl,
$R^3$ represents CN,
$R^4$ represents hydrogen or fluorine, and
$R^5$ represents hydrogen.

5. The method according to claim 1, wherein such synthetic pyrethroid is of the formula

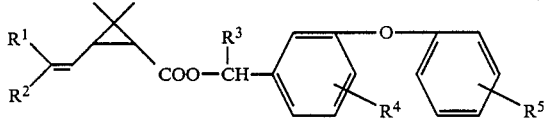

in which
$R^1$ represents chlorine,
$R^2$ represents chlorine or p-chlorophenyl,
$R^3$ represents CN,
$R^4$ represents fluorine in the 4-position, and
$R^5$ represents hydrogen.

6. The method according to claim 1, wherein such synthetic pyrethroid is cyfluthrin.

7. The method according to claim 1, wherein such synthetic pyrethroid is flumethrin.

8. The method according to claim 1, wherein the synthetic pyrethroid is painted onto or soaked or impregnated into a carrier which is placed into a beehive.

9. The method according to claim 1, wherein such synthetic pyrethroid is selected from the group consisting of permethrin, cypermethrin, cyfluthrin, cyhalothrin, deltamethrin and flumethrin.

10. In the control of parasitosis in honey bees by applying to the beehive a parasiticide which is selectively active against such parasitosis but not against said bees, the improvement wherein such parasiticide is a synthetic pyrethroid selected from the group consisting of cyfluthrin and flumethrin wherein the synthetic pyrethroid is painted onto or soaked or impregnated into a carrier which is placed into said beehive.

11. The method according to claim 10, wherein said synthetic pyrethroid is cyfluthrin.

12. The method according to claim 10, wherein such synthetic pyrethroid is flumethrin.

* * * * *